(12) United States Patent
Rakestraw et al.

(10) Patent No.: US 7,220,592 B2
(45) Date of Patent: *May 22, 2007

(54) PARTICULATE PROCESSING SYSTEM

(75) Inventors: David J. Rakestraw, Livermore, CA (US); Don W. Arnold, Livermore, CA (US); Phillip H. Paul, Livermore, CA (US)

(73) Assignee: Eksigent Technologies, LLC, Dublin, CA (US)

( * ) Notice: Subject to any disclaimer, the term of this patent is extended or adjusted under 35 U.S.C. 154(b) by 435 days.

This patent is subject to a terminal disclaimer.

(21) Appl. No.: 10/295,482

(22) Filed: Nov. 15, 2002

(65) Prior Publication Data

US 2004/0096977 A1 May 20, 2004

(51) Int. Cl.
*G01N 33/48* (2006.01)
(52) U.S. Cl. .................. 436/63; 436/52; 436/164; 436/165; 422/68.1; 422/73; 422/81; 422/82.05
(58) Field of Classification Search .......... 436/63, 436/52, 53, 164, 165, 172; 422/68.1, 73, 422/81–82, 82.05, 82.08
See application file for complete search history.

(56) References Cited

U.S. PATENT DOCUMENTS

| 3,143,691 A | 8/1964 | Hurd |
| 3,427,978 A | 2/1969 | Hanneman et al. |
| 3,923,426 A | 12/1975 | Theeuwes |
| 6,086,243 A | 7/2000 | Paul et al. |
| 6,277,257 B1 | 8/2001 | Paul et al. |
| 6,406,848 B1 | 6/2002 | Bridgham et al. ............. 435/6 |
| 2003/0091475 A1 | 5/2003 | Yu et al. ...................... 422/99 |
| 2004/0072278 A1* | 4/2004 | Chou et al. ................... 435/29 |

FOREIGN PATENT DOCUMENTS

| WO | WO 00/12123 | 3/2000 |
| WO | WO 01/38865 | 5/2001 |
| WO | WO 01/85341 | 11/2001 |
| WO | WO 03/085379 | 10/2003 |

OTHER PUBLICATIONS

Brenner, S.; et al., "Gene Expression Analysis by Massively Parallel Signature Sequencing (MPSS) on Micro Bead Arrays" Nature Biotechnology (2000) 18, 630-634.
Kitamori, T.; et al., "Integration of an Immunosorbent Assay System: Analysis of Secretory Human Immunoglobulin A onPolystyrene Beads in a Microchip" Anal. Chem. (2000), 72, 1144-1147.

* cited by examiner

*Primary Examiner*—Maureen M. Wallenhorst
(74) *Attorney, Agent, or Firm*—Jeffrey G. Sheldon; Sheldon Mak Rose & Anderson PC

(57) ABSTRACT

A system for simultaneously processing a plurality of particles, e.g. beads or cells. A liquid sample containing the particles is delivered to a processing chamber in which the particles are positioned on particle retainers which lie in a plane. The particle retainers are sized to receive only one particle, so that the particles do not overlap. The system can make use of positioning fluid for forcing the particles into the particle retainers. The positioned particles can, for example, be processed by interrogating the particles with a light of a preselected wavelength, and analyzing signals received from the particles.

5 Claims, 10 Drawing Sheets

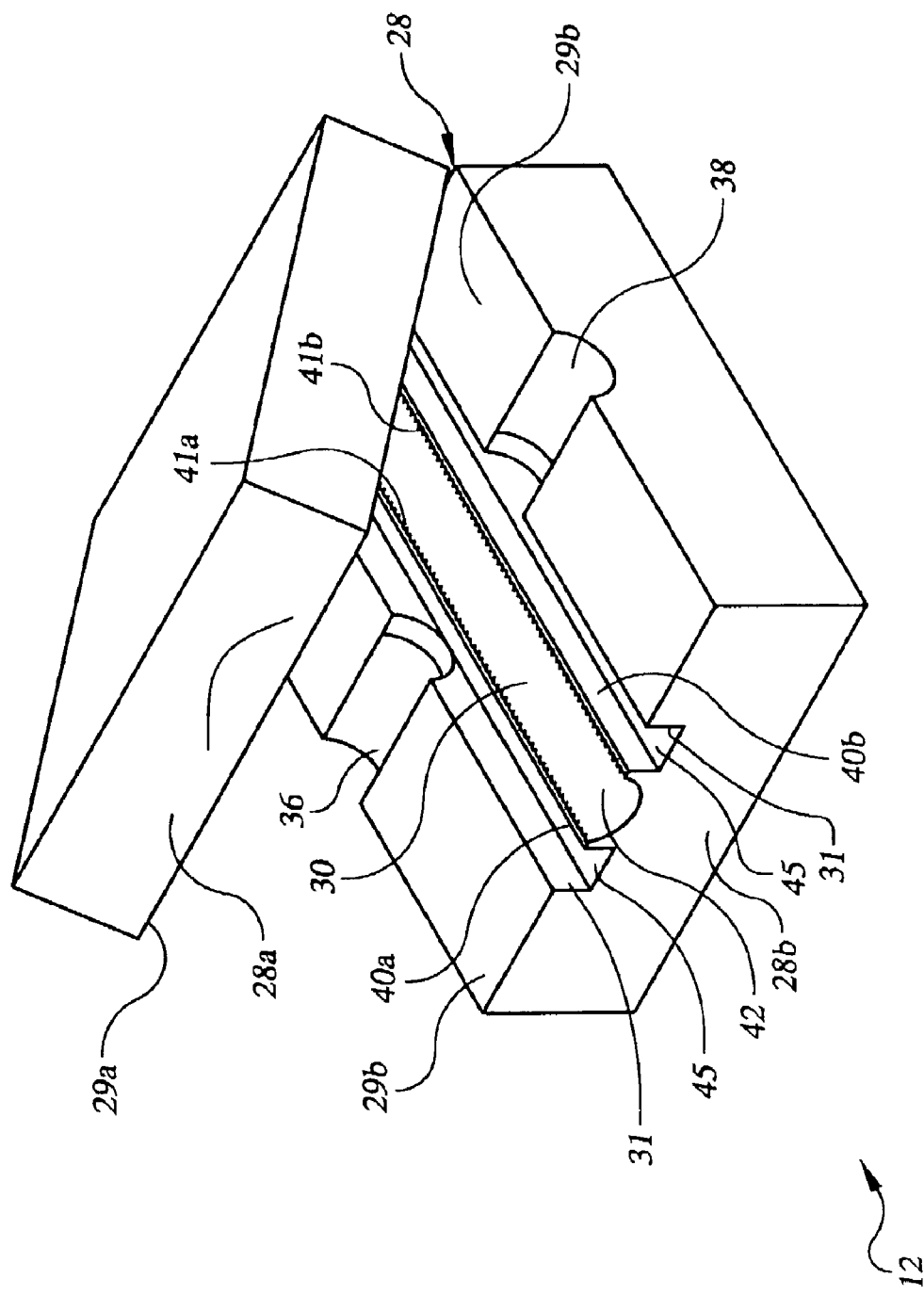

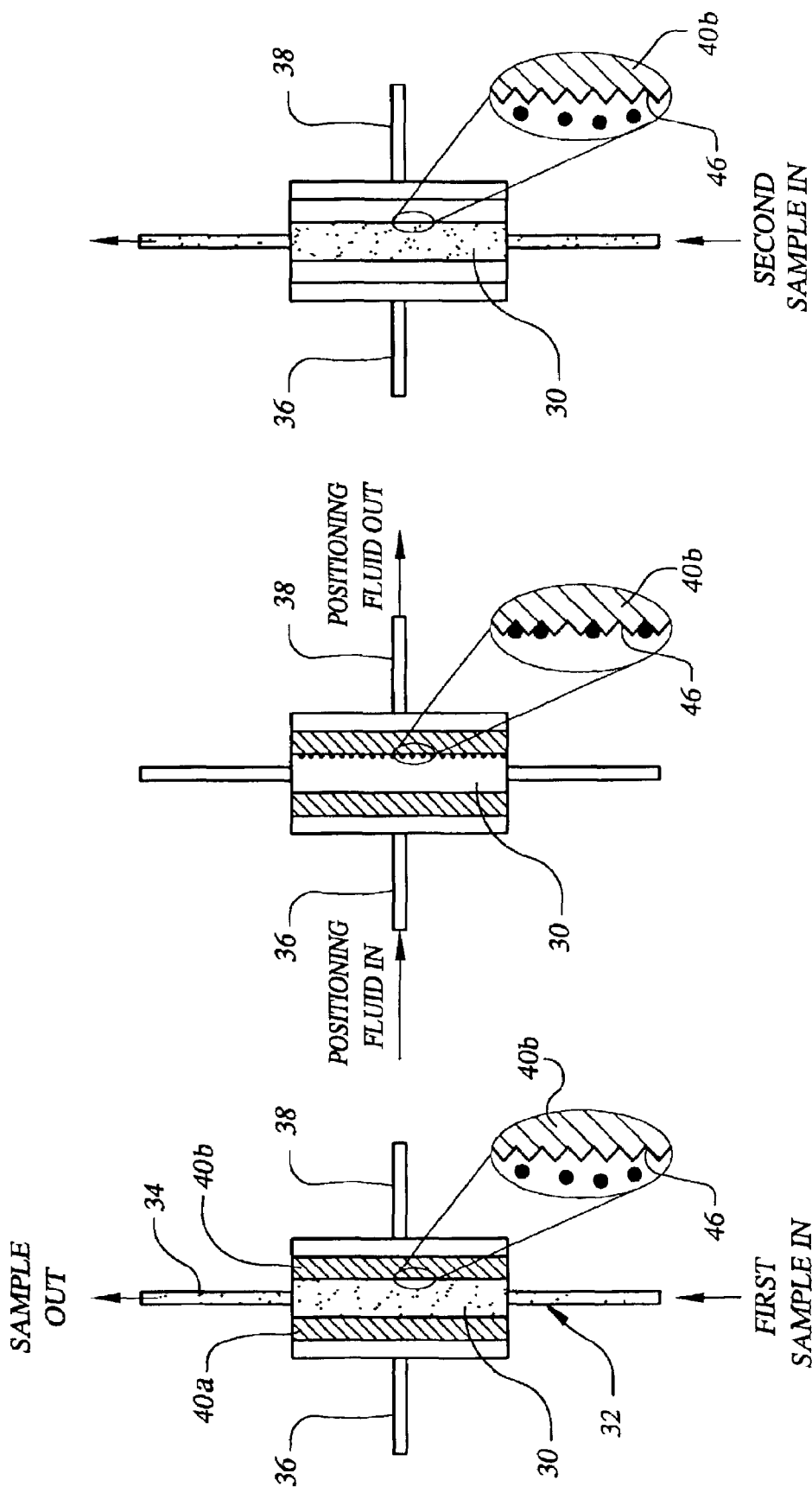

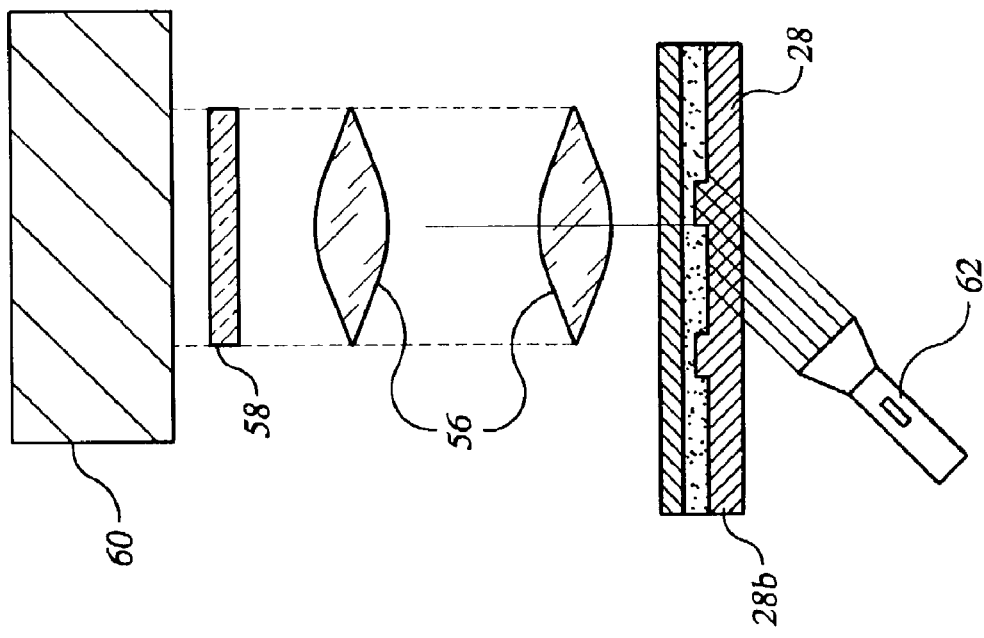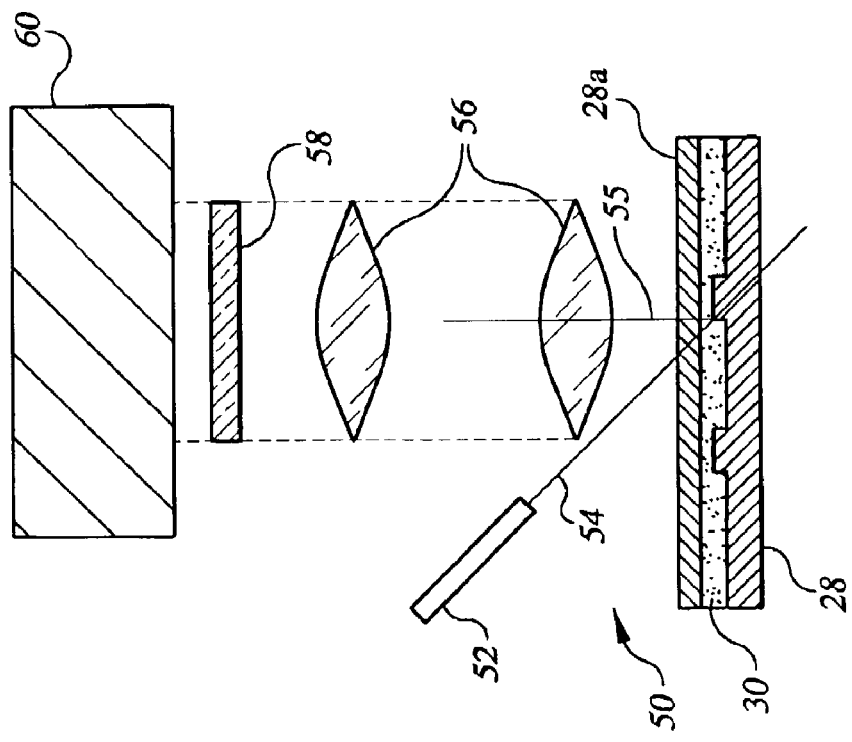

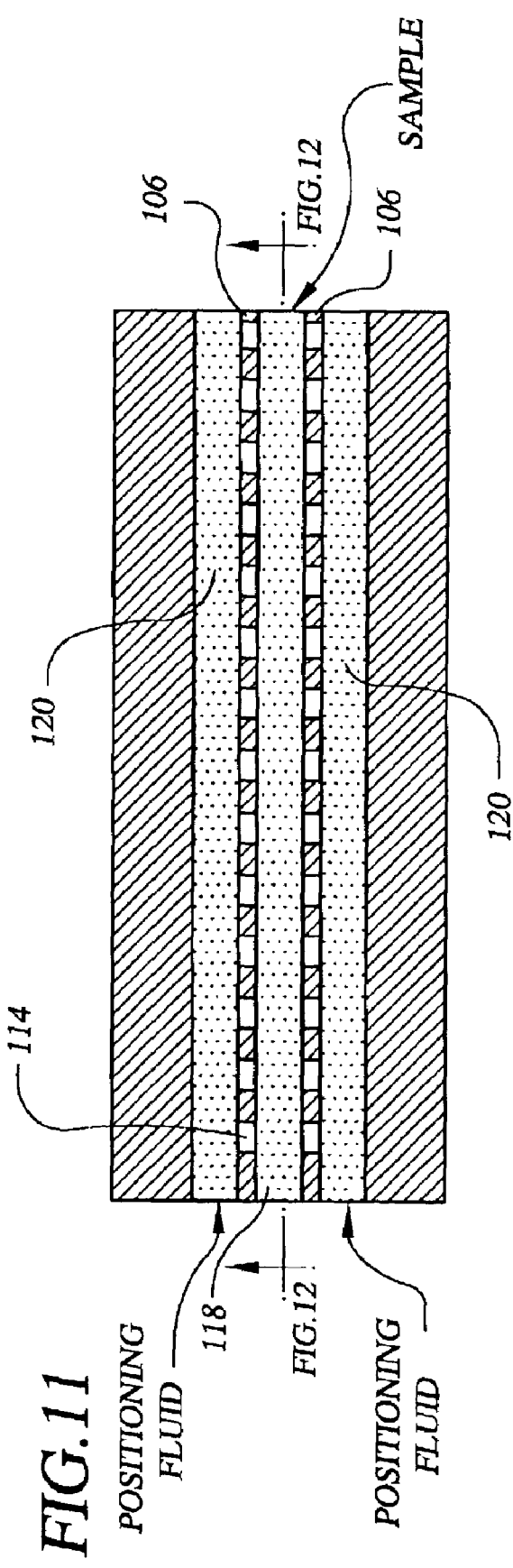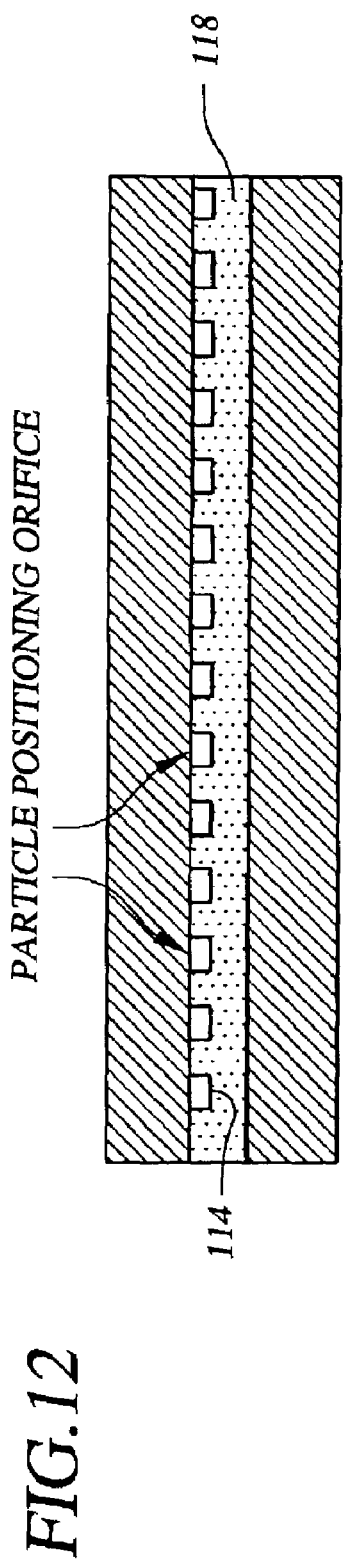

PARTICULATE PROCESSING SYSTEM

BACKGROUND

Chemical analysis is very important for life sciences research, clinical diagnostics and a wide range of environmental and process monitoring. An important class of measurements are conducted on particles such as cells or beads. For most of these application it is desirable that the analysis tools and methods be accurate, fast, easy to use and low cost.

Flow cytometry can be used for analyzing particulate elements including cells and beads, including beads having attached thereto biological materials. Exemplary flow cytometry apparatus and methods are described in U.S. Pat. Nos. 5,747,349; 5,981,180; and 6,139,800, which are incorporated herein by reference. Flow cytometry has disadvantages. For example the particles to be analyzed need to positioned very steadily, and only one particle can be detected at a time. Thus particles need to move at a steady flow rate for accurate results, but also at very high rates for high sample throughput. To obtain accurate results under these conditions, flow cytometry utilizes sophisticated, high speed, expensive detection electronics, which results in a relatively large and expensive instrument.

Other techniques for analyzing particles are described in Brenner, S.; et al, "Gene Expression Analysis by Massively Parallel Signature Sequencing (MPSS) on Micro Bead Arrays" Nature Biotechnology (2000), 18, 630–634; and Kitamori, T.; et al, "Integration of an Immunosorbent Assay System: Analysis of Secretory Human Immunoglobulin A on Polystyrene Beads in a Microchip" Anal. Chem. (2000), 72, 1144–1147.

The techniques described in these publications suffer from one or more disadvantages, such as an inability to analyze more than a single particle at a time, uncontrolled positioning of particles making analysis difficult, overlapping of particles so that the one particle interferes with the analysis of another particular, the need for all particles to have substantially the same size, and low signal to noise ratios, thereby making analysis difficult.

Accordingly, there is a need for a system for processing particles that is rapid, accurate, low cost and capable of processing multiple particles simultaneously, and that does not require all the particles to be of the same size.

SUMMARY

The present invention provides a system that satisfies this need. The system includes a processor, also referred to as an analyzer, which is used for processing a feed stream, also referred to as a sample, containing a liquid and a plurality of particulate elements. The analyzer comprises (i) a body, (ii) a process section, also referred to as an analysis section, in the body, (iii) an inlet conduit into the body, and typically (iv) an outlet conduit from the body. The inlet conduit is sufficiently large that the feed stream can flow there through into the process section. Similarly the outlet conduit is sufficiently large to remove analyzed sample from the analysis section.

The process section comprises positioning means for positioning the particles in the process section so that substantially all the particles are constrained in a predetermined location, when introduction of the feed stream into the process section is stopped. The predetermined location is well-defined. Preferably the particles are constrained so that there is substantially no overlap of the particles. The process section is contained in a plane, and the positioning means positions the particulate elements so there is substantially no overlap in the plane of the process section when introduction of the feed stream into the process section is stopped. The positioning means can be a plurality of particle retainers, such as pockets or conduits through a weir, sized to receive the particulate elements, each particle retainer being sized to receive only one particulate element at a time. The particle retainers only temporarily retain the particulate elements, and thus, are configured to allow a retained particulate element to be removed therefrom.

The positioning means can also include means for selectively forcing the particulate elements into the particle retainers. As an example, the particulate elements can include a magnet responsive element and the analyzer comprises a magnet for selectively forcing particulate elements into the particle retainer. Alternatively the particulate elements can be electrically charged and the analyzer can include an electric field generator for forcing the particulate elements into the particle retainers.

Preferably the positioning means comprises a positioning fluid for selectively forcing particulate elements, into the particle retainer, where the body has a positioning fluid inlet and a source of positioning fluid that is introduced to the positioning fluid inlet. In this version of the invention, the body can have positioning fluid outlet for removing positioning fluid from the process section. Preferably the process section has a structure such as a weir, a porous material, vias, or posts that prevents the particulate elements from leaving the process section through the positioning fluid outlet.

The particulate elements can be processed by any technique found in the art, as is appropriate for the specific particulate elements being processed, including analysis of particles by use of a light source for producing a signal. The light source provides light of a selected wavelength and to which the particulate elements respond by producing a signal. The particulate elements can have a label such as a fluorescent dye to produce a light signal. A detector is used to detect the signal from the particulate elements.

An analyzer according to the present invention can have multiple process sections, each being provided with its own sample inlet conduit and sample outlet so that a large numbers of particles can be analyzed simultaneously.

In a method according to present invention (a) a feed stream is introduced into the analyzer through the inlet conduit to flow into the process section; (b) a first set of particulate elements is positioned in a predetermined location such as in the particle retainers; and (c) analyzed therein. The analyzed particles are then released, and steps (a) through (c) are repeated with additional sets of particulate elements.

The analyzer can include a control system for introducing sample intermittently, in defined time intervals, and intermittently positioning the particulate elements at the predetermined location for analysis.

Thus, according to the present invention a large number of particulate elements can be processed at one time, where the particulate elements do not interfere with the analysis of each other, in a system that provides a high signal to noise ratio, and that is fast, inexpensive, and efficient.

DRAWINGS

These and other features, aspects and advantages of the present invention will become better understood with regard to the following description, appended claims, and accompanying drawings where:

FIG. 2 is a perspective view of the particle processor of FIG. 1;

FIGS. 6A, 6B and 6C show the sequential operation of the processor of the system of FIG. 1 where each figure includes a detailed view of a section of pockets;

FIGS. 7A and 7B show two systems for interrogating particles in a system according to the present invention;

Figure 9:
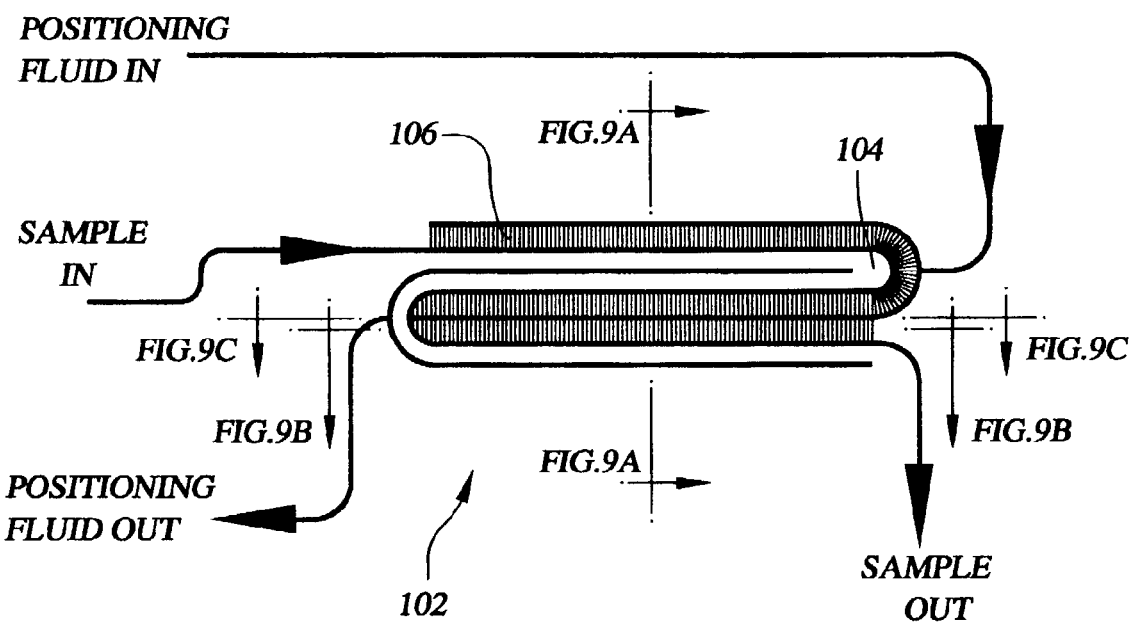
FIG. 9 is a schematic view of another version of a processor according to the present invention utilizing a serpentine flow path.
Figure 9A:
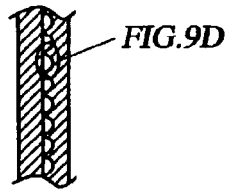
Figure 9B:
Figure 9C:
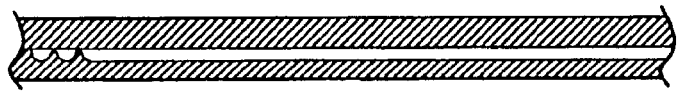
Figure 9D:
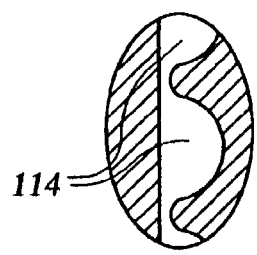
Figure 9E:
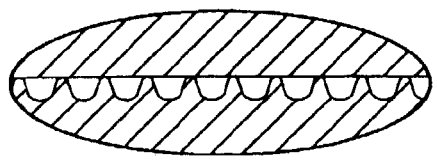
Figure 10:
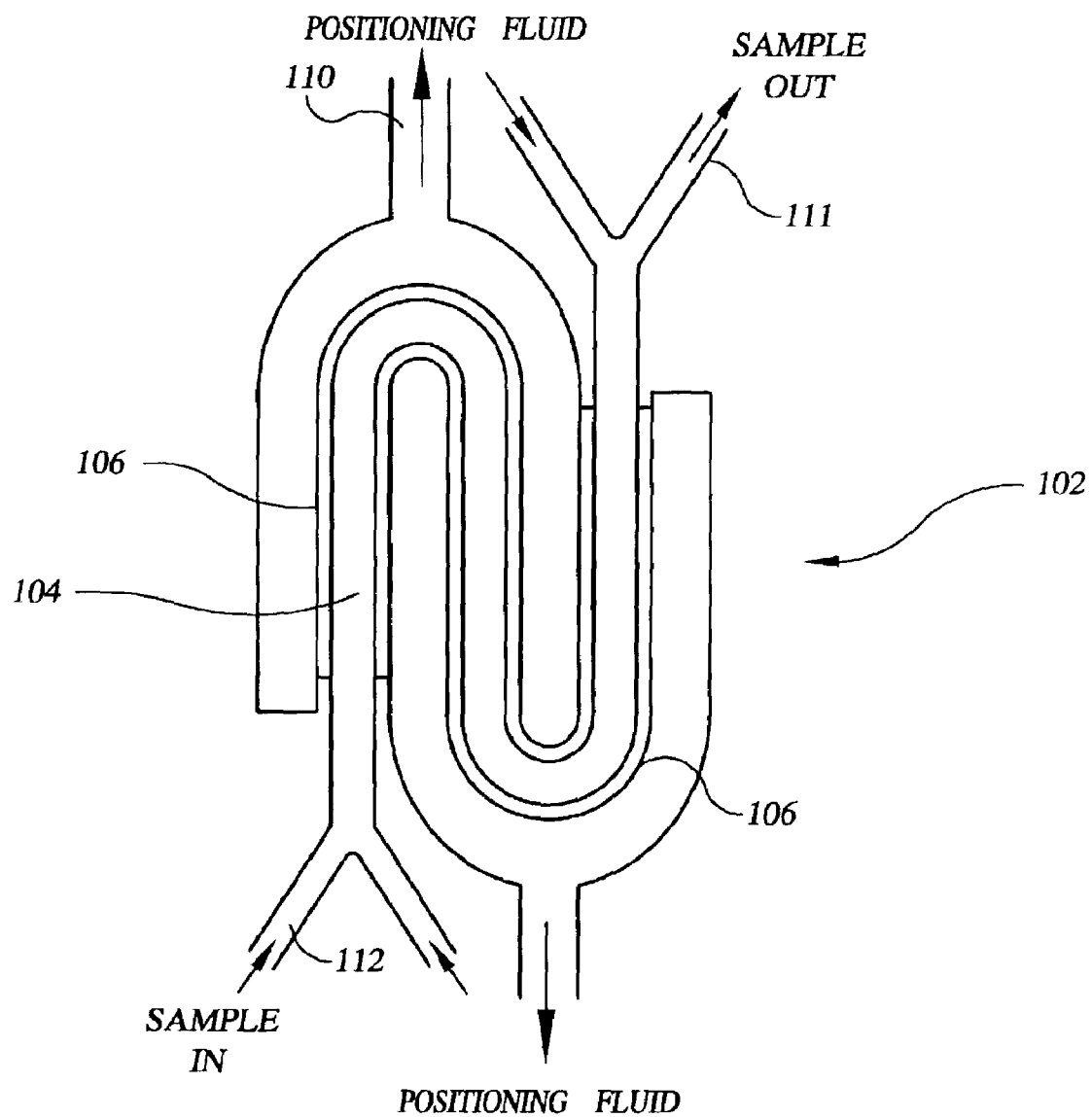
Figure 13:
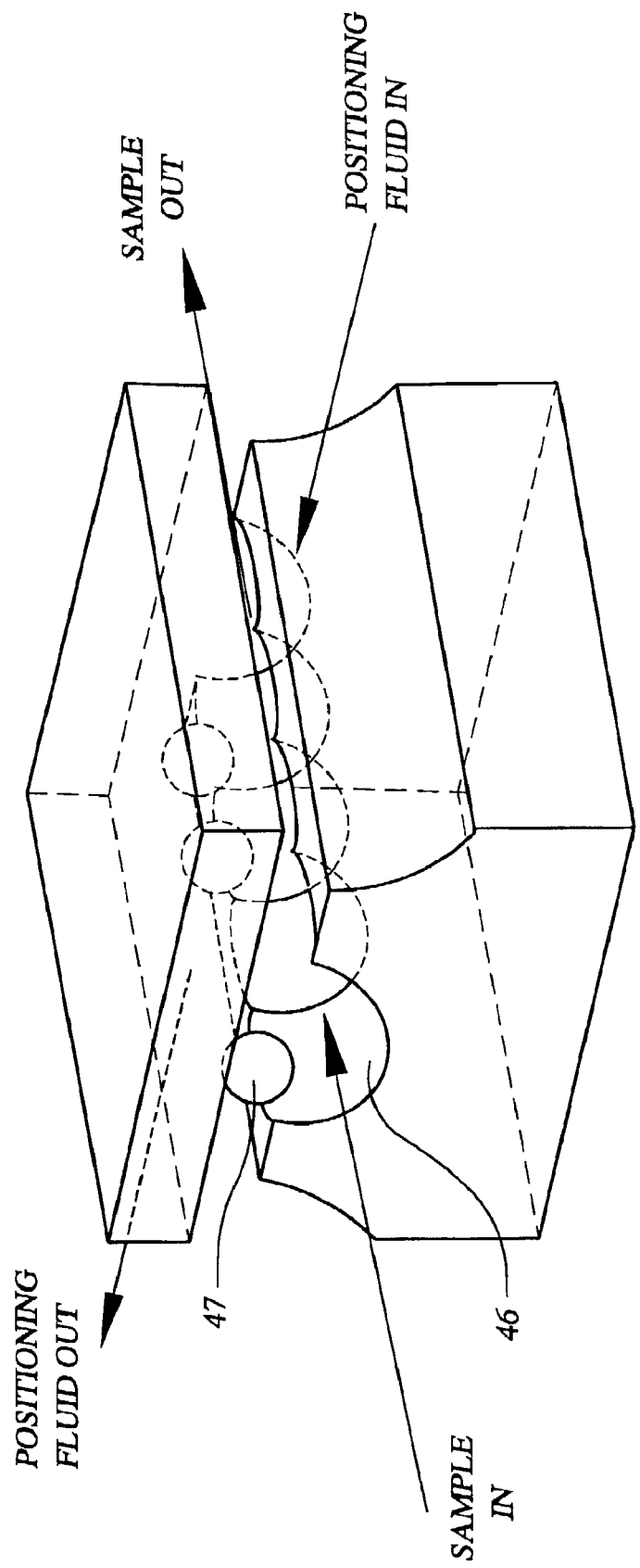

FIGS. 9A, 9B, and 9C are sectional views of the processor of FIG. 9 taken on lines 9A—9A, 9B—9B, and 9C—9C respectively, in FIG. 9;

FIGS. 9D and 9E show details of particle retainers of the processor of FIG. 9;

FIG. 10 is a schematic view of another version of an processor according to the present invention, also utilizing a serpentine flow path;

FIG. 11 is a top plan view which schematically shows a processor according to the present invention utilizing orifices or channels as the particle retainers;

FIG. 12 is a side elevation view schematically showing the processor of FIG. 11, taken on line 12—12 in FIG. 11; and FIG. 13 shows the details of particles being retained in pockets.

DESCRIPTION

Figure 1:
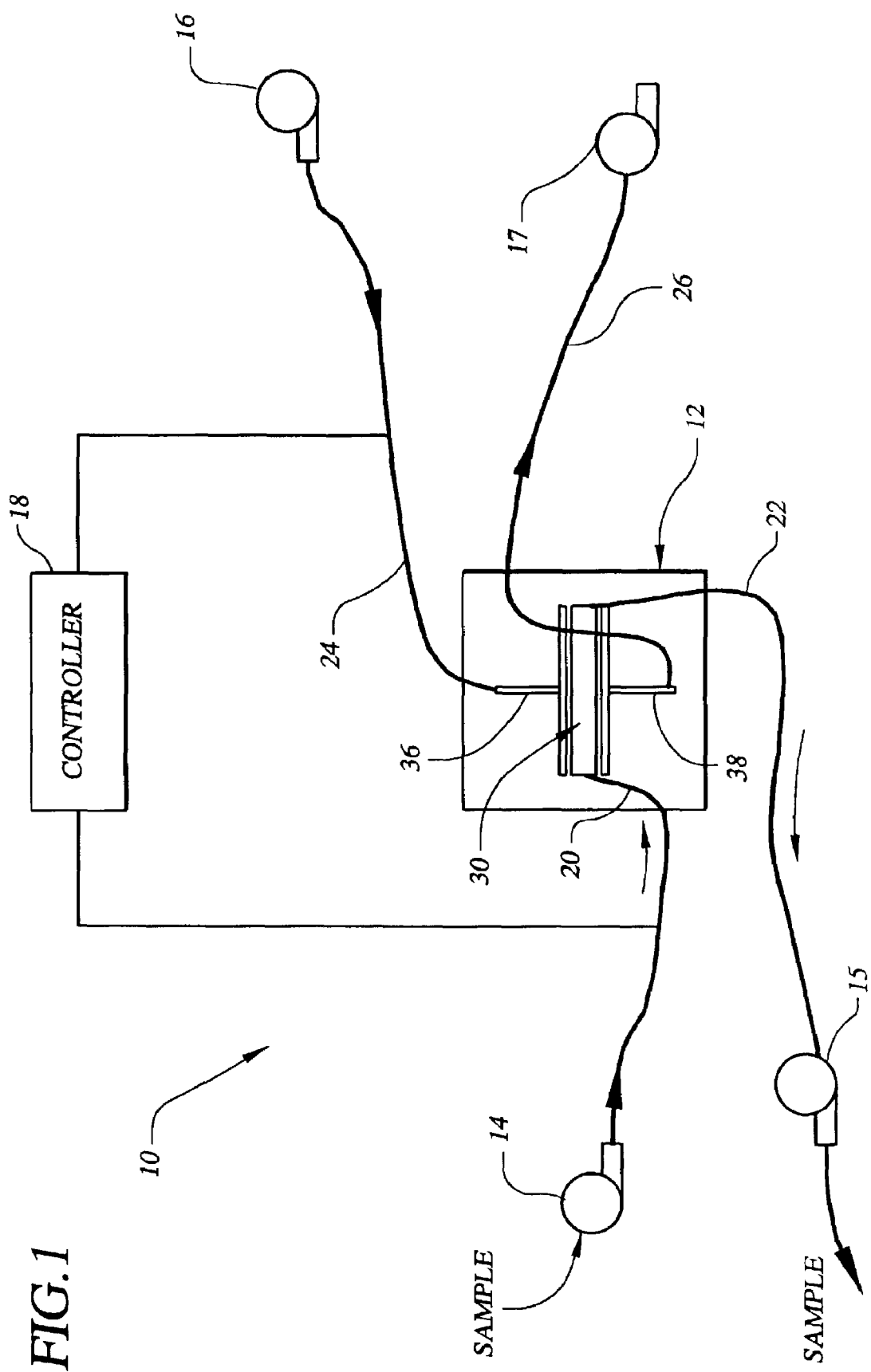
FIG. 1 is a schematic view of a system according to the present invention that includes a particle processor.
Figure 4:
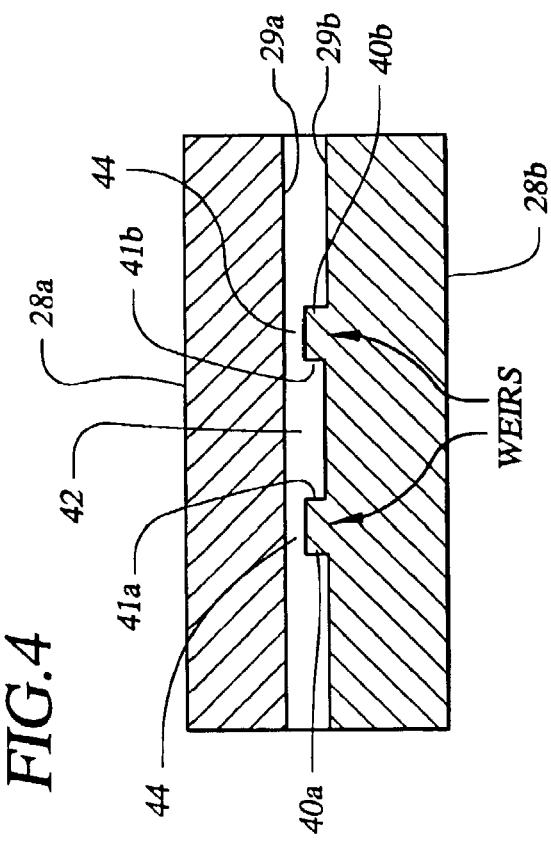
FIG. 4 is a schematic sectional view of the processor of FIG. 1 taken on line 4—4 in FIG. 3.

The present invention provides a system for analyzing a plurality of particulate elements simultaneously, quickly, efficiently, and at low cost. FIG. 1 shows an exemplary system 10 according to the present invention. The system comprises a processor 12, also referred to as an analyzer 10, a sample inlet pump 14, a sample outlet pump 15, a first positioning fluid pump 16, a second positioning fluid pump 17, and a controller 18. A sample containing particles is introduced to the analyzer 12 by introducing means, such as the sample inlet pump 14 through a sample inlet line 20 and withdrawn from the analyzer 12, after analysis, through a sample outlet line 22 in communication with the sample outlet pump 15. As described in more detail below, a positioning fluid can be used for positioning particles in the analyzer 12 for analysis. The first positioning fluid pump 16 can introduce the positioning fluid into the analyzer 12 through a positioning fluid inlet line 24 and the second positioning fluid pump 17 can withdraw positioning fluid from the analyzer 12 through a positioning fluid outlet line 26. The controller 18 controls the operation of the four pumps 14, 15, 16 and 17, and the sample detection apparatus (described below) to achieve a sequence of repeatedly and intermittently introducing sample into the analyzer, positioning particles, analyzing positioned particles and withdrawing positioning fluid and analyzed particles from the analyzer, in a predetermined series of steps.

A portion of an analyzer 12 that exemplifies some of the features of the present invention is shown in more detail in FIGS. 2–5. The analyzer 12 comprises a body 28 that is formed with a top element 28a and a bottom element 28b that have substantially the same perimeter dimensions. The top 28a has a bottom surface 29a that mates with a top surface 29b of the bottom 28b. After fabrication of the top 28a and bottom 28b, they are sealed together with such a means as chemical bonding. The analyzer 12 also includes an analysis section or chamber 30 having opposed side walls 31; a sample inlet conduit 32 in fluid communication with the sample inlet line 20 and the analysis chamber 30; a sample outlet conduit 34 in fluid communication with the sample outlet line 22 and the analysis chamber 30; a positioning fluid inlet conduit 36 in fluid communication with the positioning fluid inlet line 24 and the analysis chamber 30; and a positioning fluid outlet conduit 38 in fluid communication with the sample outlet line 22 and the analysis chamber 30.

Figure 3:
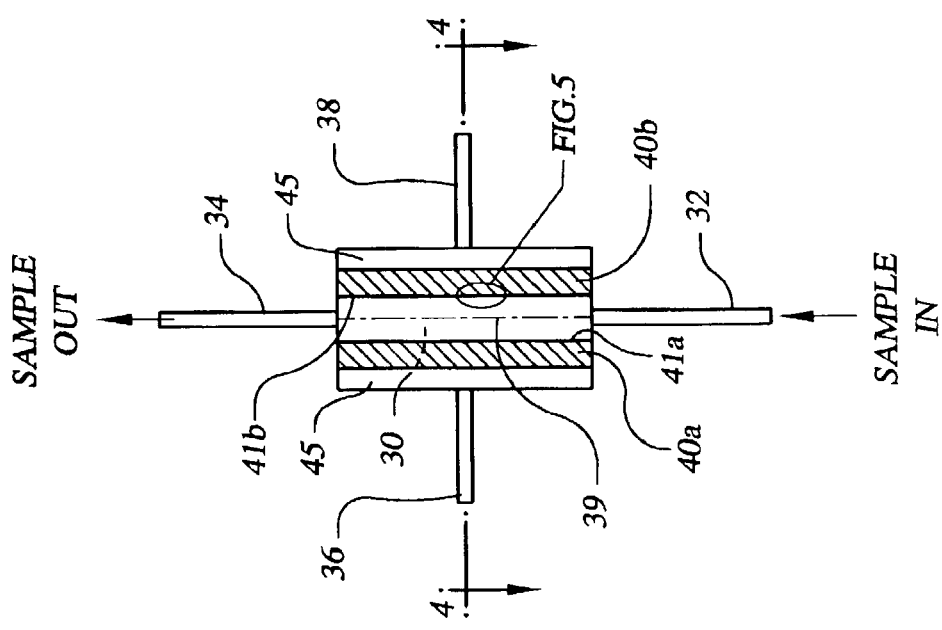
FIG. 3 is a schematic top view of the processor of FIG. 1.

The analysis chamber 30 is elongated, having a longitudinal flow path and a longitudinal axis 39 as shown in FIG. 3. The sample inlet conduit 32 and the sample outlet conduit 34 are aligned to be substantially co-axial with the longitudinal axis 39 of the analysis chamber 30. The positioning fluid inlet conduit 36 and positioning fluid outlet conduit 38 are oriented substantially perpendicular to the longitudinal axis 39 of the analysis chamber 30 so that the flow of positioning fluid is in a direction transverse, and typically substantially perpendicular, to the direction of flow of sample fluid through the analyzer 12.

The analysis chamber 30 has particle retainers such as a pair of weirs 40a and 40b that extend parallel to the longitudinal axis 39 of the analysis chamber 30 and serve to define a flow channel 42 for the sample. The weirs 40a and 40b have opposed side walls 41a and 41b respectively. The weirs 40a and 40b are sized so that particles in the sample cannot pass over the weirs, although liquid in the sample and the positioning fluid can pass over the weirs. Thus, with reference to FIG. 4, a gap 44 between the top of each weir 40 and the bottom surface 29a of the top 28a is sufficiently small, and preferably smaller than one-half the smallest dimension of particles in the sample, that the particles cannot pass through the gaps 44.

The positioning fluid inlet 36 and outlet 38 are constructed to provide relatively uniform flow across the entire interface area where they contact the analysis chamber. The positioning fluid inlet and outlet include flow diffusers 45 which assure that positioning fluid flow is uniform across the entire interfacial area in contact with the analysis chamber. Each flow diffuser 45 is essentially an elongated channel defined by one of the weirs 40 and one of the analysis chamber side walls 31.

For ease of illustration, all of features of the analyzer, including the analysis chamber 30, the sample inlet conduit 32, the sample outlet conduit 34, the positioning fluid inlet conduit 36, the positioning fluid outlet conduit 38, the weirs 40, and the flow diffusers 45 are shown as formed only in the bottom 28b of the body 28. Fabrication of analyzers with features in both the top 28a and bottom 28b of the body can also be accomplished with standard fabrication techniques.

Figure 5:
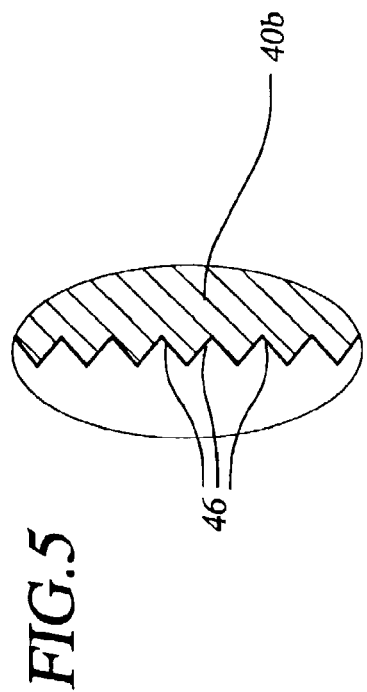
FIG. 5 is a detailed view of area 5 in FIG. 3 of the processor of FIG. 1.

As shown in FIG. 5, a plurality of particle retainers, which are pockets 46 in this version of the invention, are provided in the side wall 41b of the weir 40b. The pockets 46 are sized so that only one particle fits into a pocket for accuracy in analysis. The pockets are positioned to retain the particles in a well defined plane that is parallel with the plane formed by the interface of top 28a and bottom 28b of the body. Generally the pockets 46 are sized to be at least 5%, and more preferably at least 10%, larger than the maximum dimension of the particles being analyzed. The pocket size preferably is less than twice the smallest dimension of the particles to prevent two particles from settling into the same pocket. Generally the pockets are of a maximum depth of about 2 to about 20 microns, and a width of about 3 to about 15 microns. The number of pockets is generally from about 100 to about 1500. Preferably the pockets are spaced next each other as close as possible subject to fabrication techniques, to analyze the maximum number of particles at one time. As shown in FIG. 6, the pockets are substantially directly opposite the inlet flow of positioning fluid from the positioning fluid inlet conduit 36. Optionally pockets 46 can be on the inwardly facing surfaces of both weirs wherein the function of the positioning fluid inlet conduit and positioning fluid outlet conduit can be intermittently reversed, i.e., switched, to accelerate the analysis of particles, or through magnetic or electrical positioning (as described below), particles can be positioned in both sets of pockets.

FIG. 13 shows details of pockets 46 being used for retaining particles 47, with the particles 47 about to be forced into a pocket.

The analyzer 12 can be fabricated from many different materials, including silicon, glass, silicate, silicone, quartz and other ceramics, plastics, elastomers, and metals. When the particles are analyzed by a light source at a selected wavelength, a portion of the analyzer 12 proximate to the pockets needs to be substantially transparent to the incoming analysis light, and also to any light produced by the reaction of the particles to the incoming light. The term "substantially transparent" means that at least 60% of indirect light reaches the particles, and at least 40% of light from the particles passes through the analyzer.

The features in the analyzer body 28, such as the conduits, the analysis chamber and the pockets, can be prepared by many of known fabrication techniques, including machining, laser machining, injection molding, embossing, wet chemical etching, dry chemical etching, water jet machining, and bead jet abrasive machining.

The sample conduits 32 and 34 are sufficiently large that particles can freely flow there through. Generally the smallest dimension is at least 100% larger than the largest dimension of the particles. In an exemplary embodiment, the conduits are semicylindrical in shape, because they are formed only in the bottom 28b of the body 28, and have a width of about 75 microns and a depth of about 50 microns. The advantages of small sized conduits include the ability to rapidly introduce and position particles with minimal amounts of fluid and to maximize the number of conduits in a single analyzer 12 to provide a high rate of particle analysis. However if the conduits are too small, it is possible for them to be clogged by large particles and/or create substantial resistance to flow which increases the requirement on the pumps 14, 15, 16, and 17.

The analysis chamber 30 typically has the same depth as the sample conduits 32 and 34, and a width of about 40 to about 100 microns. In a typical system, the analysis chamber has a depth of about 10 to about 50 microns.

Figure 8:
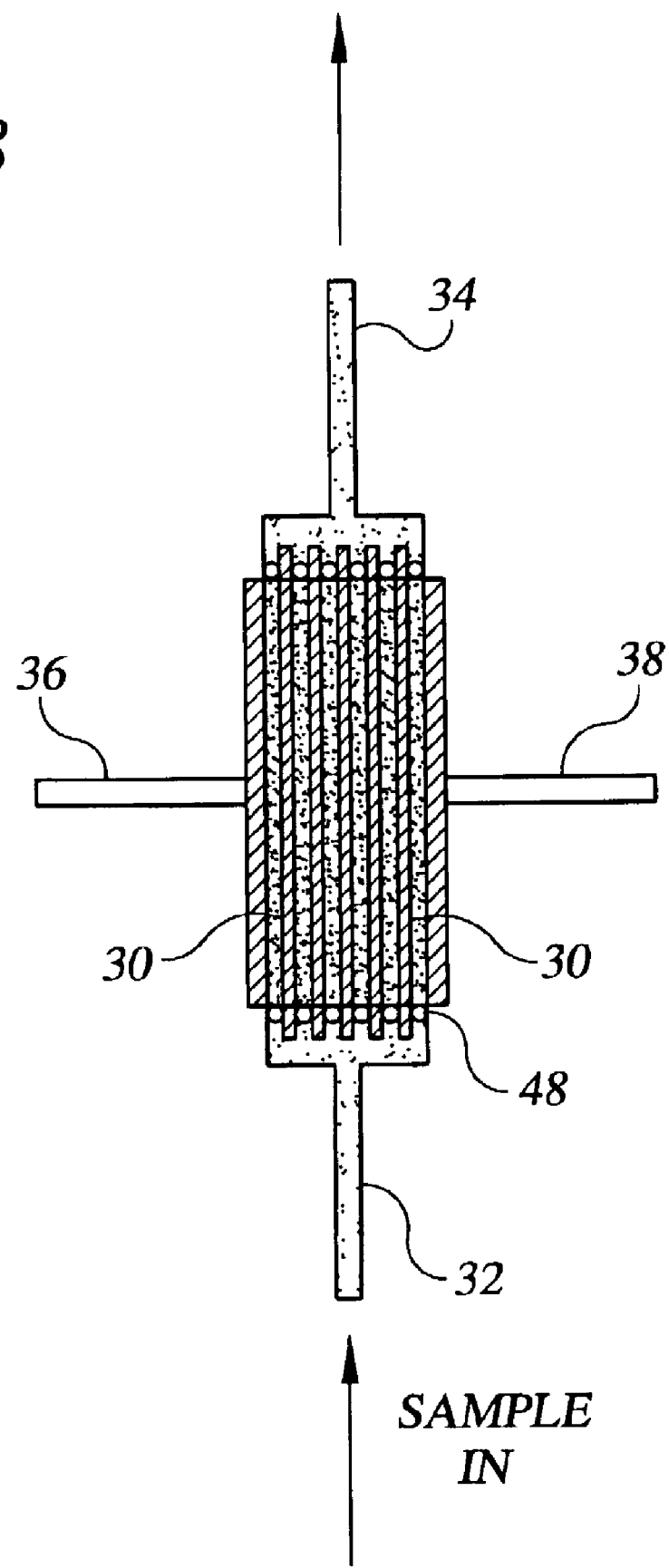
FIG. 8 shows an processor according to the present invention having multiple processing chambers.

As shown in FIG. 8, the analyzer 12 can include a plurality of parallel analysis chambers 30 each provided with its own valved inlet conduit and outlet conduit, for fast analysis. The particles can be analyzed simultaneously in the chamber. To insure relatively uniform distribution of sample through the analyzer chamber 30, a plurality of valves 48 can be used. Exemplary of the type of valves that are suitable for this are micro valves such as mobile monolith valves as described in U.S. patent application Ser. No. 09/695,816, filed on Oct. 24, 2000, which is incorporated herein by reference, and electrokinetic actuated diaphragm valves as described in U.S. Pat. No. 6,019,882, which is incorporated herein by reference, and piezo actuated diaphragm valves.

The pumps 14, 15, 16 and 17 can be electroosmotic pumps, also known as electrokinetic pumps. Electroosmotic pumps are advantageous because they can accurately introduce as low as 100 pico liters of fluid per cycle, with a precise control. Electrokinetic and electroosmotic pumps are described in U.S. Pat. Nos. 6,013,164; 6,277,257; 6,013,164; and 3,923,426, which are incorporated herein by reference. Other types of controlled pressure devices that can be used are syringe-type pumps, piezo-actuated diaphragm pumps, microbubble pumps, pneumatic pumps, peristaltic pumps or any other pump that can deliver controlled volumes of fluid as necessary to manipulate the particulate-laden suspension in the analysis device.

With reference to FIGS. 6A, 6B and 6C, the system 10 operates as follows, preferably under control of the controller 18:

Step 1—As shown in FIG. 6A, the sample pump 14 introduces sample into the analysis chamber 30 through the sample inlet line 20 and sample inlet conduit 32, at the same time the sample outlet pump 15 withdraws analyzed sample through the sample outlet conduit 34 and sample outlet line 22. The first and second positioning fluid pumps 16 and 17 are not operated during step 1. Preferably, the pumps 16 and 17 are resistant to flow in the off state, which prevents passage of fluid through the positioning fluid inlet conduit 36 and outlet conduit 38.

Step 2—As shown in FIG. 6B, the sample inlet pump 14 and the sample outlet pump 15 are stopped and the first and second positioning fluid pumps 16 and 17 are used to direct positioning fluid through the analysis chamber 30 via the positioning fluid lines 24 and 26 and the positioning fluid conduits 36 and 38. The amount of positioning fluid used does not need to equal the volume of the analysis chamber. It can be more or less. Because the sample pump 14 is not operating, fluid cannot exit the analysis chamber through the sample outlet conduit 34. The positioning fluid forces particles into the pockets 46. The weirs 40 prevent particles from leaving the analysis chamber, at the same time allowing positioning fluid, and entrained sample fluid to pass out of the analysis chamber through the positioning fluid outlet conduit 38 and the positioning fluid outlet line 26.

Step 3—The positioned particles in the pockets 46 are analyzed.

Step 4—As shown in FIG. 6C, the first and second positioning fluid pumps 16 and 17 are stopped and the sample pumps 14 and 15 are started, causing the next portion of sample to be loaded into the analysis chamber. Optionally the particles can be simultaneously displaced from the pockets with a displacement fluid that enters the chamber through conduit 38.

The number of particles in the analysis chamber is preferably correlated with the number of pockets 46. To be sure that all the particles find a pocket and to minimize stacking of particles, i.e., more than one particle in a pocket, preferably the number of pockets is at least about 1.5 and can be up to about 3 times the number of particles in the chamber, also referred to as a process section. Thus as shown in FIG. 6B, some of the pockets are empty during analysis.

The whole procedure can be performed rapidly, in the order of 1 millisecond for analyzing as many as 5000 beads in a single analysis chamber.

The controller can be any properly programmed microprocessor.

The positioning fluid is a liquid, and needs to be selected so that it does not adversely interact with the particles. For most biological samples, appropriate saline conditions must be satisfied as necessary.

Other methods are available for positioning the particles against the weirs 40a and 40b and into the pockets 46. With appropriate selection of substrate materials and particle suspension fluids, as known to those knowledgeable in the art of electroosmosis, the particles can be positioned with electroosmotically-driven fluid flow by application of an appropriate electric field. Alternatively, for charged particles, electrophoretic techniques can be used, where electrodes are used to apply an electric field across the chamber. For situations where particles naturally do not have a sufficient charge for electrophoretic techniques, the particles can be provided with such a charge, which is easily done in a case of bead based analysis. An advantage of electrophoretic positioning is that pockets 46 can be on both weirs 40a and 40b, and particles having opposite electrical charge can be placed in opposing sets of pockets.

Another technique that can be used is magnetic positioning, where the particles have a magnetic responsive element, such as beads with an iron coating. By application of a magnetic field to the analysis chamber, either with a natural magnet, man-made magnet, or electromagnet, the magnetic responsive particles can be forced into pockets.

By the term "means for positioning" there is meant not only the positioning fluid, natural magnets, artificial magnets, electromagnetics, and electrical field generators specifically described, but also any structure presently existing or invented in the future effective for positioning particles in a predetermined location for processing.

The particles that are analyzed can be naturally occurring material such as cells, including red and white blood cells, and cell fragments. The particles can also be a material such as silica, aluminum, metal, ceramic, and polymers. The particles can be of any type that have been used in cytometry including polystyrene latex particles, acrylate or methacrylate derived particles, hydrogel polymer particles, polymerized micelle particles, particles produced by grinding cast film, particles produced by photopolymerization of aqueous emulsion, and particles produced by solvent casting as described in U.S. Pat. Nos. 4,302,166 and 4,162,284.

Beads for cytometry typically range from about 0.1 μm to about 50 μm, and more typically from about 1 μm to about 20 μm in diameter. Their density is typically from about 0.5 to about 2 grams per milliliter. The particles need not be of the same size.

Typically such polymer-based beads are coded with detectable labels. For example, beads can be coded with one or more fluorescent labels, and can have on their surface capture agents for capturing a target analyte in sample, resulting in a detectible signal from the bead, particle or labeling coating. Preferably the particles incorporates coding indicia which enable unambiguous identification of the particle type, and consequently enables the analysis system to assign measurement signals from the particle and any specific analyte with which the bead interacts. Particle labeling or coding can be accomplished by varying detectable particle properties such as intensity of fluorescence from fluorescent dyes associated with the particles; ratios of intensities of fluorescence from multiple fluorescent dyes associated with the particles, size, shape, reflectivity, and relative number of the particles, and combinations of any of the above characteristics integrated over the entire particle or the spatial distribution of such properties within each particle. A "detectable signal" can be the absence of light, i.e., a fluorophore could be quenched so that it gives off no light. It is also possible to code the particles by adding materials with other detectable properties such as magnetic materials. Additionally information about useful coding schemes may be found in Fulwyler, U.S. Pat. No. 4,499,052; Coulter Electronics, UK Patent No. 1,561,042; and Tripatzis, European Patent No. 126450.

The target analytes can be any of a large number of materials, including:

(i) Electrolytes, i.e., ions, such as sodium, potassium, ammonium, calcium, chloride and carbon dioxide (carbonate). Electrolytes can be detected with optode particles such as disclosed in U.S. Pat. No. 6,165,790 which is incorporated herein by reference.

(ii) Small metabolite molecules, e.g., saccharides such as glucose, fructose, lactose, galactose, ammonia, urea, uric acid, cholesterol, triglycerides, ethanol, lactate, salicylate, acetaminophen, bilirubin and creatinine;

(iii) enzymes such as alkaline phosphatase, alanine aminotransferase, aspartame aminotransferase, amylase, cholinesterase, creatine kinase, alpha-amylase, gamma-glutamyl transferase, lactate dehydrogenate and lipase.

(iv) Antibodies or antigens, such as myoglobin, tropinin I, Ch-MB, and those disclosed in U.S. Pat. No. 4,665,020.

(v) Specific polynucleotide sequence of interest, e.g., a gene or messenger RNA. Examples of particles specifically adapted for analysis of DNA sequences are disclosed in Fulton, U.S. Pat. Nos. 5,736,330 and 6,057,107.

Once the particles are positioned, a variety of different light interrogation techniques can be used to identify the particles and to determine the response of the particles to the assay. For instance one or more dyes can be used, and different colors and/or different dye concentrations can be used for generating different codes from different particles. Interrogated properties can include, but are not limited to size, shape, morphology, reflectivity, fluorescence intensity, fluorescence wavelength, composition, and bound target analyte. Detection methods can be based on magnetic properties, radioactive properties, and electrochemical properties including electro chemiluminescence. For example, by patterning electrodes into the analysis chambers, voltage can be applied to the particles after they are parked in the pockets, and then it is possible to measure an electrochemical signal or electrochemically generated optical signal (i.e., through chemiluminescence) as detected with an optical detector.

FIG. 7A shows a representative analysis system 50 according to the present invention. The analysis system 50 includes a light source such as a laser 52 which directs a detecting light beam 54 having a selected wavelength band width through the top 28a of the body 28 to impinge on particles in the analysis chamber 30. Light 55 is reflected or emitted from the particles, passes through appropriate optics 56 and filters 58 to be detected in a detector 60. A suitable system is described in U.S. Pat. No. 6,271,042 which is incorporated herein by reference. Preferably the cross sectional area illuminated by the light 54 closely matches the cross sectional area of the trapped particles.

Alternatively, as shown in FIG. 7B, a diffused light source such as a LED device 62 can be used. Although such light sources are inefficient for interrogating a single particle such as in flow cytometry, they can be used efficiently in the present invention where the larger cross sectional area associated with an array of particles can be interrogated in parallel. Also as shown in FIG. 7B, the light source can introduce light through the bottom 28b of the body 28.

Although FIGS. 7A and 7B illustrate the use of a single light source, the use of multiple light sources in parallel can be implemented.

Among the detection devices 60 that can be used are CCD cameras, CID cameras, diode arrays, and photographic film. The filters 58 can be used for taking images of different colors by changing filters or using a tunable filter or using a multitude of filters in parallel. This allows use of multiple, different wave light sources, and multiple, different wavelength labeled particles.

For each detection position defined by the pockets 46, the detector 60 collects a signal relating to one or more interrogated properties from the particles in the pockets. High throughput is achieved because multiple particles are analyzed simultaneously. The signal from the particles can be captured in a time frame in the order of milliseconds to seconds and the data can be analyzed while the sample is removed from the chamber and a new sample is positioned for analysis, which again can take place in the order of milliseconds. By analyzing thousands of particles simultaneously with this method, very high sample analysis rate can be achieved.

In some instances, a detection system may not be needed, in that a human can visually inspect the particles for distinguishing characteristic of interest.

As shown in FIGS. 9 and 10, the analysis chamber can define a flow path which includes a non-linear portion, which can be serpentine, to yield a compact device. Thus an analyzer 102 can include a serpentine process section 104 having a serpentine flow path, where weirs 106 and diffusers are likewise serpentine. This design allows many parallel rows of particles to be formed in close proximity to each other. The closely spaced parallel rows can then be effectively imaged using two-dimensional detectors. In the version of the invention shown in FIG. 10, the positioning fluid can be introduced not only into its own inlet 110, but can also be introduced into a sample outlet 111 and sample inlet 112 in order to position particles on both walls of the analysis chamber.

Instead of using pockets as the particle retainers, as shown in FIGS. 9A–9E, 11 and 12, an analyzer can use a sieve formed of a plurality of properly sized conduits 114 through weirs 106 to retain particles for analysis. As shown in FIGS. 11 and 12, instead of using a weir where liquid flows over it along the entire length of the weir as shown in FIG. 2, the weirs 106 can have a plurality of closely spaced conduits 114 that connect an analysis chamber 118 with diffusers 120. Thus the conduits 114 serve as the particle retainers. The cross-section of the conduits 114 is smaller than the smallest particle. An advantage of this version of the invention is that a wide range of particle sizes can be used. With pockets, the maximum size of particles is limited by the pocket size. In this version of the invention, the conduit size does not provide an upper limit on the particle size. For example, 2×2 micron conduits can trap any particle larger than 2 microns. Preferably, the conduit size will be less than ½ the size of the smallest dimension of the smallest particle to prevent the particles from partially fitting in the conduit.

In a dynamic system according to the present invention, assays can be conducted while the particles undergo dynamic change while they are positioned for detection in the chamber. For example the composition of fluid that is in contact with the particles can be altered to induce chemical or physical changes to the particles, any species bound to the particles or the binding interaction of the species and the particles. Through proper interrogation methods it is possible to carry out kinetic measurements by monitoring the particles and/or a bound species as a function of time.

With reference to FIGS. 6A, 6B and 6C, the system 10 operates dynamically as follows, preferably under control of the controller 18:

Step 1—As shown in FIG. 6A, the sample pump 14 introduces sample into the analysis chamber 30 through the sample inlet line 20 and sample inlet conduit 32, at the same time sample outlet pump 15 withdraws analyzed sample through the sample outlet conduit 34 and sample outlet line 22. Preferably, the pumps 16 and 17 are resistant to flow in the off state which prevents passage of fluid through the positioning fluid inlet conduit 36 and outlet conduit 38.

Step 2—As shown in FIG. 6B, the sample pump 14 and the sample outlet pump 15 are stopped and the positioning fluid pump 16 and the positioning fluid outlet pump 17 are used to introduce positioning fluid into the analysis chamber 30 through the positioning fluid inlet line 24 and the positioning fluid inlet conduit 36. Because the sample pump 14 is not operating, fluid cannot exit the analysis chamber through the sample outlet conduit 34. The positioning fluid forces particles into the pockets 46. The weirs 40 prevent particles from leaving the analysis chamber, at the same time allowing positioning fluid, and entrained sample fluid to pass out of the analysis chamber through the positioning fluid outlet conduit 38 and positioning fluid outlet line 26. In the dynamic mode of operation, the positioning fluid contains an analyte, reactant, substrate, etc., that interacts with the particle or some chemical or biological species present on the surface of or in the interior of the particle in some meaningful way that is correlated with an attribute that is being probed. The interaction produces, if the desired attribute is present, a change that is detectable through any of the aforementioned methods.

Step 3—The positioned particles in the pockets 46 are monitored as a function of time, using the detection method appropriate, for the changes that occur upon positive (or negative) interaction between the particle-based and the positioning-fluid entrained species as described in Step 2. Changes in the detected signal for each particle are monitored as the analyte is flowed over the particle in the particle positioning fluid stream. Time-dependent interrogation in the chamber can provide additional real-time kinetic and dynamic information about the interactions.

Step 4—As shown in FIG. 6C, the positioning fluid pump 16 and the positioning fluid outlet pump 17 are stopped and the sample pump 14 and sample outlet pump 15 are started, causing the next portion of sample to be loaded into the analysis chamber. Optionally the particles can be displaced from the pockets with a displacement fluid that enters the chamber through conduit 38.

The system of the present invention has many advantages. It can operate on a micro scale, thereby needing only very small sample volumes. It provides rapid, sensitive and inexpensive analysis of particles, allowing multiple particles to be interrogated simultaneously without interference from other particles. In addition, it is possible to interrogate a single particle at one time, and thus the present invention is not limited to analyzing multiple particles simultaneously.

Although the present invention has been described in considerable detail with reference to certain preferred versions thereof, other versions are possible. For example, the system of the present invention has many uses in addition to analyzing particles. For example, it can be used for chemical synthesis using particles as a solid phase support in which the synthesis occurs. It is particularly useful for a synthesis involving a reaction that can be monitored in real time. The small volume of the analysis chamber minimizes the volume of reagent that is required, and the sequential steps of a reaction can be carried out in one or more analysis chambers, utilizing the positioning fluid conduit for providing different reagents. As an example, a serial four-chamber system can sequentially apply guanine, cytosine, thymine, and adenosine into the chambers for oligonucleotide synthesis. Similarly, the system can be used for sample preparation, pre-concentration, extraction and clean up. Discrimination for low-concentrations of target analytes and high background analyte concentrations can be achieved by passing a sample over capture particles positioned in the analysis chamber. Accordingly, the scope of the appended claims should be limited to the description of the preferred versions contained herein.

All documents cited herein are incorporated herein by reference in their entirety. All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112, unless to sustain the validity of the claim.

What is claimed is:

1. A method of simultaneously processing multiple particles which have different sizes, the method comprising the steps of
   (A) pumping a sample from a pump site into a processing chamber through an unbranched inlet conduit which extends from the pump site to the processing chamber; the sample:
      (a) having a controlled volume which is the same when the sample leaves the pump site and when it enters the processing chamber, and
      (b) comprising
         (i) a liquid, and
         (ii) multiple particles which have different sizes and which are dispersed in the liquid; and
   wherein the processing chamber contains a plurality of particle retainers, the particle retainers lying in a plane, and each particle retainer having a size such that one, but only one, of each of the particles can be retained therein;
   (B) causing the particles in the sample to be received by the particle retainers; and
   (C) simultaneously processing the particles received by the particle retainers;
      wherein each of the particle retainers is a pocket having a size which is (i) at least 10% larger than the maximum dimension of any of the particles and (ii) less than twice the smallest dimension of any of the particles: and,
   wherein the pockets are placed on a weir, and there is a gap above the weir through which liquid can pass and which has a maximum dimension which is less than half the smallest dimension of the particles.

2. Apparatus suitable for carrying out the method of claim 1, the apparatus comprising:
   i. a pump site which comprises a pump and at which a sample comprising a liquid and multiple particles dispersed in the liquid can be prepared;
   ii. a processing chamber containing a plurality of particle retainers, the particle retainers being formed on a weir and lying in a plane, and each particle retainer having a maximum depth of about 2 to about 20 micron and a width of about 3 to about 15 micron; and,
   iii. an unbranched inlet conduit which extends from the pump site to the processing chamber and through which a sample prepared at the pump site can be pumped into the processing chamber.

3. Apparatus according to claim 2 further comprising means for directing a positioning fluid through the processing chamber.

4. Apparatus according to claim 2 further comprising a light source for illuminating particles retained in the particle retainers, and a detector for detecting signals from particles illuminated by the light source.

5. A method of simultaneously processing multiple particles which have different sizes, the method comprising the steps of:
   (A) pumping a sample from a pump site into a processing chamber through an unbranched inlet conduit which extends from the pump site to the processing chamber; the sample:
      (a) having a controlled volume which is the same when the sample leaves the pump site and when it enters the processing chamber, and
      (b) comprising:
         (i) a liquid, and
         (ii) multiple particles which have different sizes and which are dispersed in the liquid; and
   the processing chamber containing a plurality of particle retainers the number of particle retainers being about 1.5 to about 3 times the number of particles in this sample, the particle retainers lying in a plane, and each particle retainer having a size such that one, but only one, of each of the particles can be retained therein;
   (B) causing the particles in the sample to be received by the particle retainers; and
   (C) simultaneously processing the particles received by the particle retainers;
   wherein each of the particle retainers is a pocket having a size which is (i) at least 10% larger than the maximum dimension of any of the particles and (ii) less than twice the smallest dimension of any of the particles; and,
   wherein the pockets are placed on a weir, and there is a gap above the weir through which liquid can pass and which has a maximum dimension which is less than half the smallest dimension of the particles.

* * * * *